United States Patent
Watanabe et al.

(10) Patent No.: US 9,835,598 B2
(45) Date of Patent: Dec. 5, 2017

(54) LIQUID SENDING PIPE FOR LIQUID CHROMATOGRAPH DETECTOR AND LIQUID CHROMATOGRAPH

(71) Applicant: SHIMADZU CORPORATION, Kyoto-shi, Kyoto (JP)

(72) Inventors: Masato Watanabe, Kyoto (JP); Masahide Gunji, Kyoto (JP)

(73) Assignee: SHIMADZU CORPORATION, Kyoto-shi, Kyoto (JP)

(*) Notice: Subject to any disclaimer, the term of this patent is extended or adjusted under 35 U.S.C. 154(b) by 661 days.

(21) Appl. No.: 14/012,227

(22) Filed: Aug. 28, 2013

(65) Prior Publication Data
US 2014/0060163 A1 Mar. 6, 2014

(30) Foreign Application Priority Data
Aug. 30, 2012 (JP) .................. 2012-190484

(51) Int. Cl.
*G01N 30/30* (2006.01)
*G01N 30/62* (2006.01)

(52) U.S. Cl.
CPC ........ *G01N 30/30* (2013.01); *Y10T 137/6416* (2015.04)

(58) Field of Classification Search
CPC .. G01N 30/30; G01N 2030/626; G01N 30/62; G01N 30/20; G01N 35/10; G01N 230/626
See application file for complete search history.

(56) References Cited

U.S. PATENT DOCUMENTS

| | | | | |
|---|---|---|---|---|
| 2,002,241 A | * | 5/1935 | Forde | F27D 11/02 219/390 |
| 2,375,714 A | * | 5/1945 | Wild | F25D 23/123 165/63 |
| 3,864,909 A | * | 2/1975 | Kern | F01N 3/26 285/41 |
| 3,903,868 A | * | 9/1975 | Salvo | F24H 1/24 122/136 R |

(Continued)

FOREIGN PATENT DOCUMENTS

| | | |
|---|---|---|
| CN | 101379393 A | 3/2009 |
| JP | 07-318489 A | 12/1995 |

(Continued)

OTHER PUBLICATIONS

Chinese Office Action dated Oct. 10, 2014 in Chinese Patent Application No. 201310389258.0, English translation.

(Continued)

*Primary Examiner* — John Fitzgerald
(74) *Attorney, Agent, or Firm* — Sughrue Mion, PLLC

(57) ABSTRACT

A heat insulating member 13 is provided on the outer circumference of a connection pipe 11. The heat insulating member 13 includes: a tube 12; and an air layer 15 between the connection pipe 11 and the tube 12. Accordingly, it is possible to always keep the temperature of a sample component at the time of detection by a detector constant and thus prevent an influence of the temperature on an output result of the detector, in a low flow rate analysis using a modularized column unit and a modularized detection unit.

4 Claims, 3 Drawing Sheets

(56) References Cited

U.S. PATENT DOCUMENTS

| | | | | |
|---|---|---|---|---|
| 4,220,136 | A | * | 9/1980 | Penney ............... F24J 2/0015 126/600 |
| 4,269,710 | A | * | 5/1981 | Hunt ..................... G01N 30/30 210/198.2 |
| 4,370,826 | A | * | 2/1983 | Davidson ............. E06B 3/2605 49/118 |
| 5,039,409 | A | * | 8/1991 | Blaffert ................ G01N 30/88 210/198.2 |
| 5,283,995 | A | * | 2/1994 | Richter ................. E06B 3/685 52/202 |
| 5,529,624 | A | * | 6/1996 | Riegler ................. C04B 28/02 106/675 |
| 7,681,369 | B2 | * | 3/2010 | Soltesiz ............... E06B 3/6604 52/204.593 |
| 2008/0047208 | A1 | * | 2/2008 | Soltesiz ............... E06B 3/6604 52/204.595 |
| 2010/0223978 | A1 | * | 9/2010 | McCauley .................. 73/23.37 |
| 2011/0120213 | A1 | * | 5/2011 | Hirayama et al. .......... 73/61.55 |
| 2011/0186157 | A1 | * | 8/2011 | Paul et al. ............. 137/565.01 |
| 2011/0302994 | A1 | * | 12/2011 | Anderson et al. ........... 73/23.35 |

FOREIGN PATENT DOCUMENTS

| | | |
|---|---|---|
| JP | 08-129004 A | 5/1996 |
| JP | 2003-207491 A | 7/2003 |
| JP | 2008-032544 A | 2/2008 |
| JP | 2008-256530 A | 10/2008 |
| JP | 2010-048554 A | 3/2010 |
| JP | 2011-013151 A | 1/2011 |
| SU | 1332112 A * | 5/1986 |

OTHER PUBLICATIONS

Communication dated Aug. 18, 2015 from the Japanese Patent Office in counterpart application No. 2012-190484.

Chinese Office Action dated May 11, 2015 in corresponding Chinese Patent Application No. 201310389258.0, English translation.

* cited by examiner

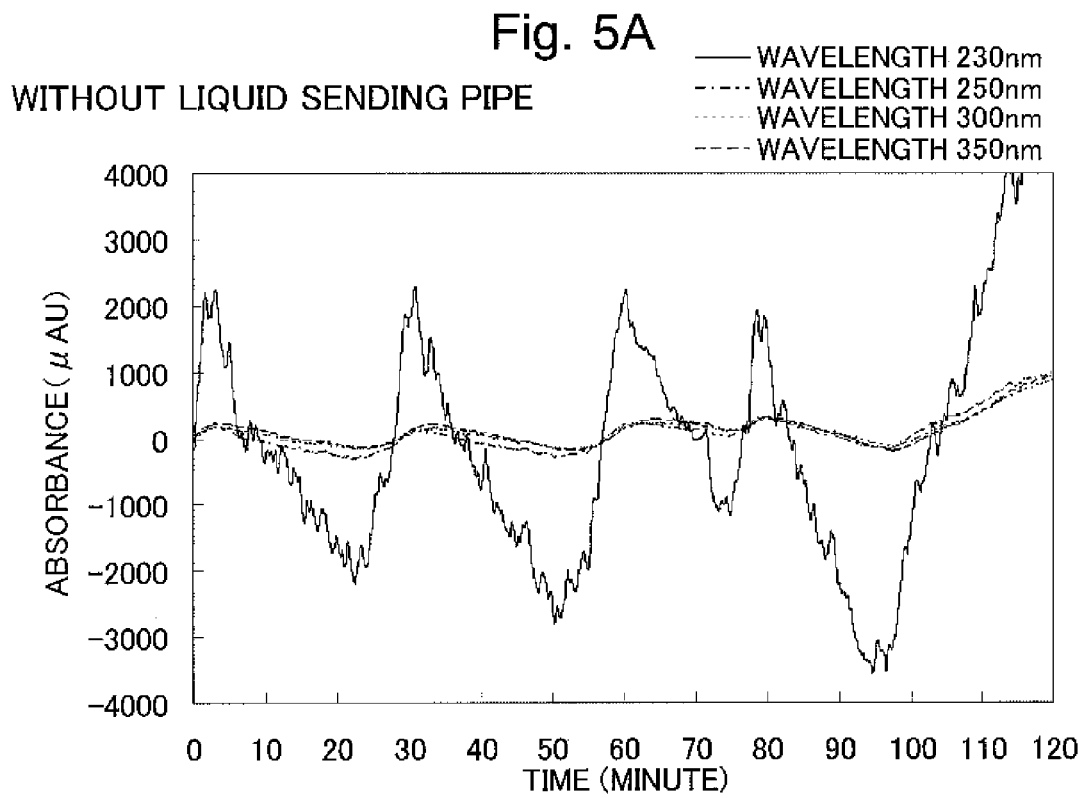
Fig. 5A  WITHOUT LIQUID SENDING PIPE
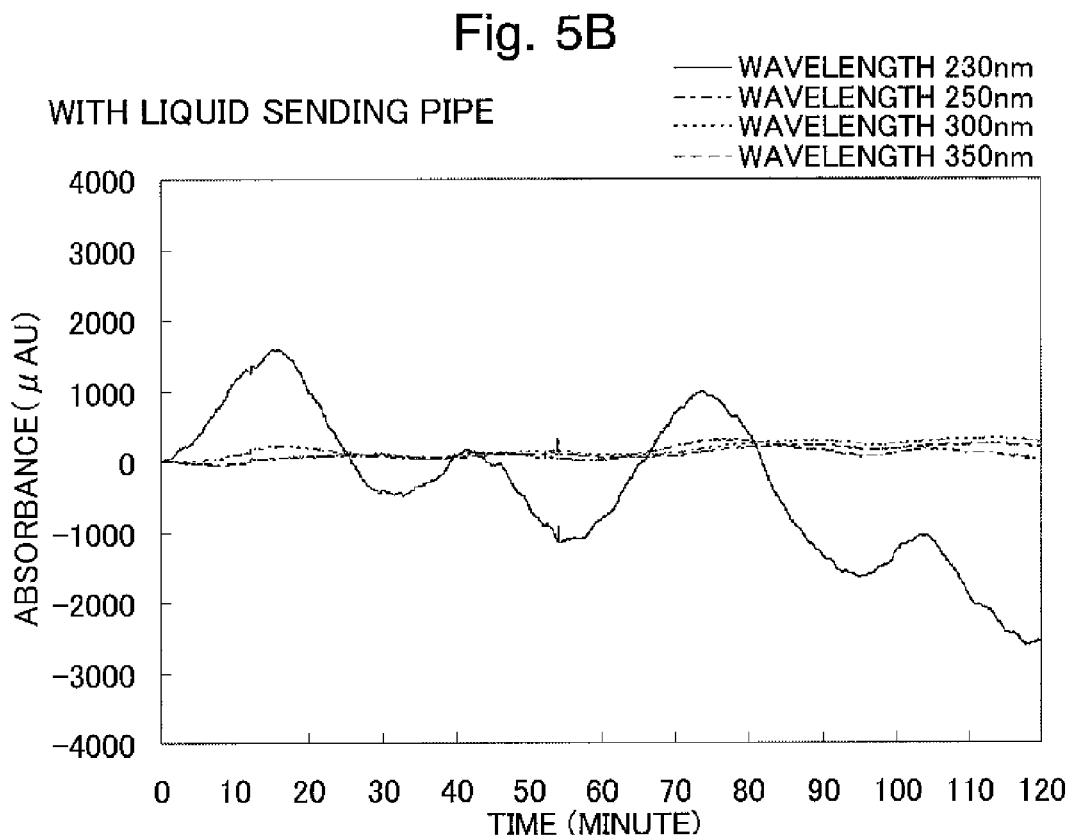
Fig. 5B  WITH LIQUID SENDING PIPE

LIQUID SENDING PIPE FOR LIQUID CHROMATOGRAPH DETECTOR AND LIQUID CHROMATOGRAPH

TECHNICAL FIELD

The present invention relates to a liquid sending pipe for a liquid chromatograph detector and a liquid chromatograph.

BACKGROUND ART

In a liquid chromatograph, a sample is injected into a column, and components of the sample are temporally separated using a difference in the affinity and a distribution state of the components of the sample to two phases of a stationary phase and a mobile phase. Each component is eluted from the column, then passes through a pipe together with the mobile phase, and is introduced into a detector to be subjected to an analysis.

Various methods are applied to the detector. At present, especially optical detectors such as an absorbance detector and a fluorescence detector are most frequently applied for reasons of a wide application range thereof and the like.

Light absorption characteristics and the like of a sample component are susceptible to temperature. Hence, if the temperature of the mobile phase containing the sample component changes, the output of the detector is influenced by the change in temperature, so that correct analysis results cannot be obtained. In the case where the mobile phase is influenced by a temperature fluctuation in a relatively long cycle, the influence appears as a change in baseline of the detector output. In the case where the mobile phase is influenced by a temperature fluctuation in a cycle shorter than a change in baseline, the influence appears as noise. In order to avoid such influences, the temperature of the sample component (that is, the temperature of the mobile phase) at the time of detection by the detector needs to be kept constant.

Hence, temperature control of constituent parts of the liquid chromatograph from the column to the detector is important. In the liquid chromatograph, normally, the column and the detector are each modularized, modules suited to an analysis purpose are selected and combined, and the modules are connected by a pipe, whereby desired performance is obtained. The temperatures of the modularized column and the modularized detector are controlled independently of each other.

For example, JP-A 2010-48554 discloses a technique of controlling the temperature of a column. According to this technique, the column is housed inside of a constant temperature bath, and a temperature sensor is attached to the outer surface of the column. Electric current supplied to a heater provided in the constant temperature bath is controlled such that a value of the temperature sensor is a target temperature, whereby the temperature of the column (that is, the temperature of a mobile phase) is controlled.

Further, JP-A 2008-256530 discloses a technique of controlling the temperature of a detector. According to this technique, a flow cell is irradiated with light emitted from a light source, and the amount of transmitted light is detected by a photodetector. This configuration includes: a sample temperature regulation block for housing the flow cell therein; and a photodetector temperature regulation block for housing the photodetector therein, and also includes a simultaneous temperature regulation block in contact with the two blocks. Then, the simultaneous temperature regulation block is regulated to a constant temperature, whereby the temperature of a mobile phase supplied to the flow cell and the temperature of the photodetector are kept constant.

As described above, a pipe is necessary to send a mobile phase containing a sample from a column module to a detector module, and the temperature of the mobile phase fluctuates under influences of surrounding environments also when the mobile phase passes through the pipe between the column module and the detector module. In view of the above, conventionally, as shown in FIG. 4, a pipe winding unit 42 is provided in the detector module separately from a pipe 41, and the pipe winding unit 42 is placed in close contact around a temperature regulation block. A region sandwiched between two double wavy lines in FIG. 4 shows the inside of a temperature regulation block 46, where a light source 45, a flow cell 43, and a photodetector 44 are provided.

In this configuration, even if the temperature of the mobile phase is changed by influences of surrounding environments when the mobile phase passes through the pipe 41 between a column module 47 and a detector module 40, the temperature of the mobile phase is made constant by heat exchange with the temperature regulation block and the like when the mobile phase passes through the pipe winding unit 42. Accordingly, the temperature of the mobile phase supplied to the flow cell 43 is always constant, and the output of the photodetector 44 can be prevented from being influenced.

BACKGROUND ART DOCUMENT

Patent Document

[Patent Document 1] JP-A 2010-48554
[Patent Document 2] JP-A 2008-256530

DISCLOSURE OF THE INVENTION

Problems to be Solved by the Invention

In recent years, in high-performance liquid chromatographs (HPLCs), great importance is placed on a reduction in flow rate of a mobile phase, in order to reduce consumption of the mobile phase and a sample. Conventionally, the lowest flow rate is about several microliters/minute, whereas the flow rate is required to be reduced to about one tenth of several microliters/minute in recent years.

If the flow rate of the mobile phase is reduced, the heat capacity of the mobile phase passing through a pipe between a column module and a detector module decreases, and influences of surrounding environments thereon increase. In the configuration of FIG. 4, because the heat capacity of the mobile phase is small, the temperature of the mobile phase detected by the detector is more stable.

Meanwhile, unfortunately, the amount of mobile phase is increased by the long pipe winding unit 42, the analysis time is longer, and the sample component spreads in a flow path direction, which causes a problem of peak broadening.

An objective of the present invention is to provide a liquid sending pipe for a liquid chromatograph detector and a liquid chromatograph that are capable of always keeping the temperature of a sample component at the time of detection by the detector constant and thus preventing an influence of the temperature on the output of the detector, in a low flow rate analysis using a modularized column unit and a modularized detection unit.

Means for Solving the Problems

The present invention achieved to solve the aforementioned problems provides a liquid sending pipe for a liquid chromatograph detector, the liquid sending pipe being used for a liquid chromatograph including: a column module in which a column is housed in a temperature-regulated constant temperature bath; and a temperature-regulated detection unit module, the liquid sending pipe including:

a) a connection pipe for introducing a sample eluted from the column of the column module into the detection unit module; and b) a heat insulating member for covering an outer circumference of the connection pipe.

The heat insulating member may include: an air layer for covering the outer circumference of the connection pipe; and a tube for covering the air layer. With this configuration, an excellent heat insulating effect of air can be used.

The heat insulating member may include a sealing member for sealing the air layer between the connection pipe and the tube. With this configuration, the air between the connection pipe and the tube is not lost, and new air does not enter from the outside, so that the heat insulating effect can be enhanced.

Further, the heat insulating member may include a sponge for covering an outer circumference of the tube, whereby a more excellent heat insulating effect can be obtained.

The invention of the present application also provides a liquid chromatograph including: a column module in which a column is housed in a temperature-regulated constant temperature bath; and a temperature-regulated detection unit module, the liquid chromatograph including:

a) a connection pipe provided between the constant temperature bath and the detection unit module; and b) a heat insulating member for covering an outer circumference of the connection pipe.

Moreover, in the liquid chromatograph, a lowest flow rate in a measurement range is equal to or less than 1 µL/min.

Effects of the Invention

With the liquid sending pipe for a liquid chromatograph detector and the liquid chromatograph according to the present invention, the temperature of the connection pipe is insusceptible to influences of surrounding environments due to the heat insulating effect of the heat insulating member that covers the outer circumference of the connection pipe. Hence, without the need to provide a pipe winding unit as in conventional cases, it is possible to always keep the temperature of a sample component at the time of detection by the detector constant and thus prevent an influence of the temperature on the output of the detector, in a low flow rate analysis.

Further, the column exterior volume (here, refers to "the volume of a flow path in which a sample component is eluted from the column and is supplied to a flow cell") can be reduced by removing the pipe winding unit. Hence, effects outside of the column, such as peak broadening, can be reduced, and an increase in speed and resolution of the liquid chromatograph can be achieved.

BRIEF DESCRIPTION OF THE DRAWINGS

FIG. 5A is a graph showing an experiment result when a liquid sending pipe of the present invention is not used, and FIG. 5B is a graph showing an experiment result when the liquid sending pipe of the present invention is used.

BEST MODES FOR CARRYING OUT THE INVENTION

Figure 1:
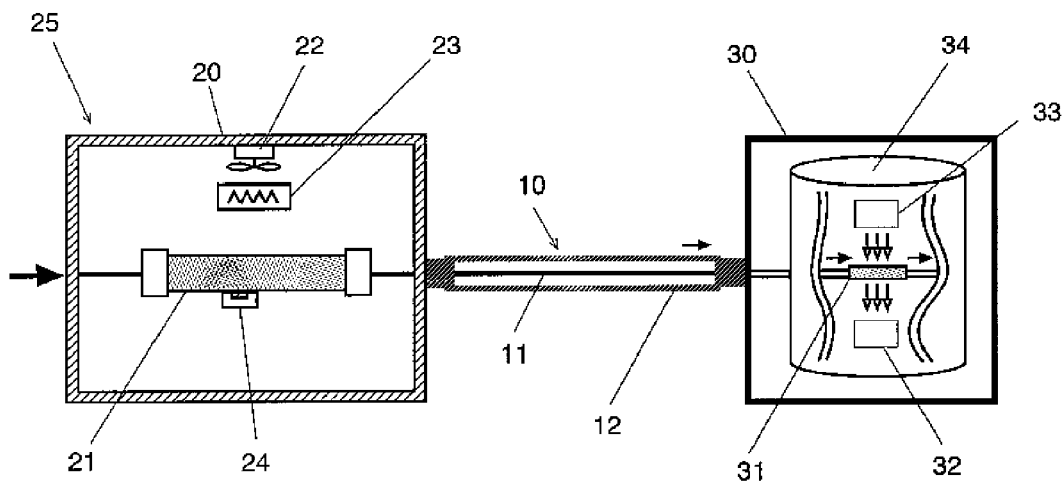
FIG. 1 is a configuration diagram of a main part of a liquid chromatograph according to an embodiment of the present invention.

Hereinafter, a liquid sending pipe for a liquid chromatograph detector according to an embodiment of the present invention is described in detail with reference to the attached drawings. FIG. 1 is a configuration diagram of a main part of a liquid chromatograph according to the present embodiment. In a configuration of a column module 25, a column 21 that separates each component of a sample is housed in a temperature-regulated constant temperature bath 20. A fan for agitation 22 and a heater for heating 23 are provided inside of the constant temperature bath 20. A temperature sensor 24 is provided on a surface of the column 21 to regulate the temperature to be constant.

A detection unit module 30 includes a temperature regulation block 34, and the temperature of the temperature regulation block 34 is regulated by a heater, a temperature sensor, and the like, which are not shown. A region sandwiched between two double wavy lines in FIG. 1 represents the inside of the temperature regulation block 34, and a light source 33, a flow cell 31, and a photodetector 32 are provided inside thereof. Sample components eluted from the column 21 and a mobile phase reach the detection unit 30 through a connection pipe 11, and are then supplied to the inside of the flow cell 31. The flow cell 31 is irradiated with light from the light source 33, the transmitted light is detected by the photodetector 32, and the detection result is converted into light absorption characteristics of the sample components. The analysis is not limited to such measurement of light absorption characteristics, but other characteristics such as fluorescence characteristics may be measured.

Figure 2:
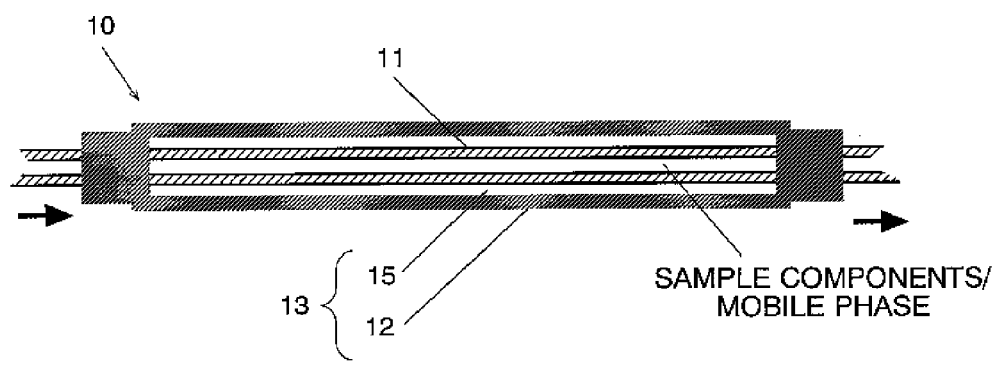
FIG. 2 is a configuration diagram of a liquid sending pipe for the liquid chromatograph detector according to the present embodiment.
Figure 3:
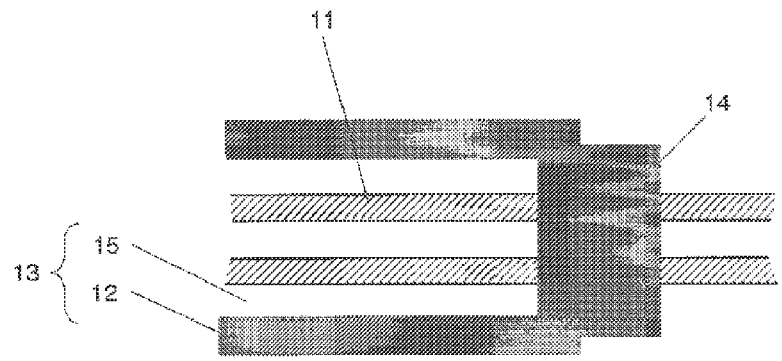
FIG. 3 is a detailed diagram of the liquid sending pipe for the liquid chromatograph detector according to the present embodiment.
Figure 4:
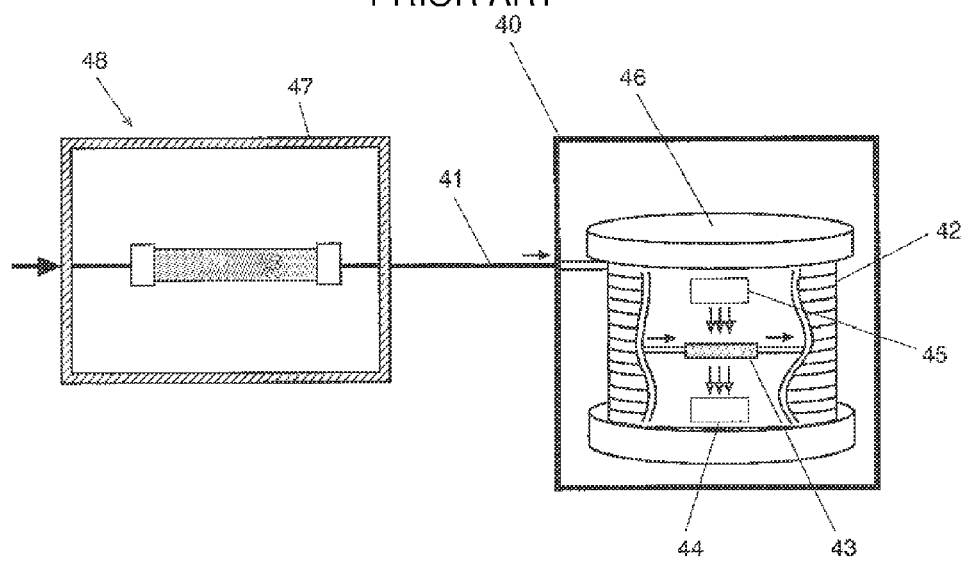
FIG. 4 is a schematic diagram of a conventional liquid chromatograph detector.

According to a configuration (liquid sending pipe 10) characteristic of the invention of the present application, an outer circumference of the connection pipe 11 between the column module 25 and the detection unit module 30 is covered with a tube 12 (FIG. 1). That is, an air layer 15 is formed between the connection pipe 11 and the tube 12, and a heat insulating member 13 made of the air layer 15 and the tube 12 is provided on the outer circumference of the connection pipe 11 (FIG. 2). Further, a sealing member 14 is provided at each end of the connection pipe 11, whereby the air layer 15 is sealed between the connection pipe 11 and the tube 12 (FIG. 3). The sealing member may be formed by, for example, using a heat-shrinkable tube as the tube 12 and heating and shrinking each end of the heat-shrinkable tube. Moreover, in order to enhance a heat insulating effect, the outer circumference of the tube 12 may be covered with a sponge or the like.

In order to check effects of the present embodiment, in a configuration without a pipe winding unit, an influence on the output of a detector of the liquid chromatograph was checked through an experiment for each of the cases where the liquid sending pipe of the invention of the present application was used and where the liquid sending pipe thereof was not used (that is, where only the connection pipe was used). In each experiment, a PEEK (registered trademark) pipe made of a resin was used as the connection pipe. Conventionally, a stainless-steel pipe having a relatively high heat conductivity (16.7 to 26.0 W/(m·k)), for example, is used for the material of the connection pipe, in order to enhance a heat exchange function. If a PEEK pipe having a heat conductivity that is about one tenth (0.25 to 0.92 W/(m·k)) of that of the stainless-steel pipe is used therefor, heat insulation properties can be enhanced. The inner diameter of the PEEK pipe was 0.13 mm, the outer diameter thereof was 1.6 mm, and the length of the pipe was 430 mm. Moreover, a Sumitube (registered trademark) that is a heat-shrinkable tube was used as the tube of the liquid sending pipe of the invention of the present application. The inner diameter of the Sumitube was 2.1 mm, the thickness thereof was 0.2 mm, and an air layer having a thickness of 0.25 mm was formed between the PEEK pipe and the Sumitube. The flow rate of the mobile phase of the liquid chromatograph was set to 0.6 mL/min. Further, the capacity of the flow cell and the capacity of the pipe from the column to the flow cell were each set to about one tenth of that in conventional techniques.

The experiments were carried out in a room. The temperature of the room during the experiments slowly changed in a cycle of approximately 30 minutes due to turning on/off of an air conditioner. The fluctuation range of the room temperature at that time was about 2° C. A solution containing acetonitrile, water, and triethylamine at a ratio of 500:500:1 was used as the mobile phase of the liquid chromatograph. Triethylamine is capable of great absorption in a short wavelength region around 230 nm, and the amount of its absorption increases as the temperature rises. Hence, the mobile phase used for the experiments of this time had an absorption wavelength at 230 nm. In order to also check an influence of the absorption wavelength of the mobile phase on analytical sensitivity, data was acquired for four cases where the light wavelength of the detector used for the analysis was 350 nm, 300 nm, 250 nm, and 230 nm.

FIG. 5A and FIG. 5B are graphs in which the horizontal axis is time (minute) and the vertical axis is an absorbance unit (AU) calculated from the detection intensity of the detector. First, experimental data when the liquid sending pipe 10 of the present invention was not used is described. In the graph of FIG. 5A, the detection intensity fluctuates in a relatively long cycle (about 30 minutes) (baseline fluctuation). This cycle is coincident with the fluctuation cycle of the room temperature, and it can be understood that the temperature of the mobile phase inside of the connection pipe 11 is influenced by surrounding environments (room temperature). It can also be understood that the detection intensity fluctuates in a cycle shorter than that of the baseline fluctuation. This is considered as noise that is generated because the temperature of the mobile phase inside of the connection pipe is influenced by local fluctuations of an air convection in the liquid chromatograph.

Further, it can be understood that particularly the baseline fluctuation and the noise are larger at the absorption wavelength (230 nm) of the mobile phase.

Next, experimental data when the liquid sending pipe 10 of the present invention was used is described. In FIG. 5B, both the baseline fluctuation and the noise are smaller than those in FIG. 5A. Table 1 shows numerical values of the baseline fluctuation and the noise in FIG. 5A and FIG. 5B. In Table 1, values of the baseline fluctuation are calculated from a difference between a local maximum value and a local minimum value of the detection intensity in each graph. Further, values of the noise are calculated on the basis of ASTM standards E1657-96, in order to eliminate an influence of the baseline fluctuation.

In Table 1, "Without liquid sending pipe" represents values when the liquid sending pipe of the invention of the present application was not used, and "With liquid sending pipe" represents values when the liquid sending pipe of the invention of the present application was used. It is confirmed that the use of the liquid sending pipe of the invention of the present application can make both the baseline fluctuation and the noise smaller, and can suppress an influence on the output of the detector. At 230 nm that is the absorption wavelength, the noise after the countermeasures is improved to be equal to or less than one fifth of that before the countermeasures, and the baseline fluctuation after the countermeasures is improved to be equal to or less than one half of that before the countermeasures, which can sufficiently satisfy practical application.

Although the flow rate of the mobile phase of the liquid chromatograph was 0.6 mL/min in the above-mentioned embodiment, it was also confirmed that similar effects were obtained at a flow rate of 1 μL/min or less.

TABLE 1

| Unit Au | Baseline fluctuation | | Noise | |
|---|---|---|---|---|
| Detector wavelength | With liquid sending pipe | Without liquid sending pipe | With liquid sending pipe | Without liquid sending pipe |
| (350 nm) | 100μ | 400μ | 8.02μ | 9.85μ |
| (300 nm) | 100μ | 300μ | 8.78μ | 9.91μ |
| (250 nm) | 200μ | 500μ | 9.59μ | 12.83μ |
| (230 nm) | 2000μ | 4500μ | 18.46μ | 96.25μ |

EXPLANATION OF NUMERALS

10 . . . Liquid Sending Pipe
11 . . . Connection Pipe
12 . . . Tube
13 . . . Heat Insulating Member
14 . . . Sealing Member
15 . . . Air Layer
20, 47 . . . Constant Temperature Bath
21 . . . Column
22 . . . Cooling Fan
23 . . . Heater for Heating
24 . . . Temperature Sensor
25, 48 . . . Column Module
30, 40 . . . Detection Unit
31, 43 . . . Flow Cell
32, 44 . . . Photodetector
41 . . . Pipe
42 . . . Pipe Winding Unit
33, 45 . . . Light Source
34, 46 . . . Temperature Regulation Block

The invention claimed is:

1. A liquid sending pipe for a liquid chromatograph detector, the liquid sending pipe being used for a liquid chromatograph including: a column module in which a column is housed in a temperature-regulated constant temperature bath; and a temperature-regulated detection unit module that does not include a pipe winding unit, the liquid sending pipe comprising:
   a) a connection pipe provided between the constant temperature bath and the detection unit module; and b) a heat insulating member for covering an outer circumference of the connection pipe wherein the heat insulating member includes:

an air layer for covering the outer circumference of the connection pipe;

a tube for covering the air layer; and a sealing member, which is provided at each end of the connection pipe, for sealing the air layer between the connection pipe and the tube.

2. The liquid sending pipe for a liquid chromatograph detector according to claim 1, wherein the heat insulating member includes a sponge for covering an outer circumference of the tube.

3. A liquid chromatograph including: a column module in which a column is housed in a temperature-regulated constant temperature bath; and a temperature-regulated detection unit module that does not include a pipe winding unit, the liquid chromatograph comprising:

a) a connection pipe provided between the constant temperature bath and the detection unit module; and b) a heat insulating member for covering an outer circumference of the connection pipe wherein the heat insulating member includes:

an air layer for covering the outer circumference of the connection pipe;

a tube for covering the air layer; and a sealing member, which is provided at each end of the connection pipe, for sealing the air layer between the connection pipe and the tube.

4. The liquid chromatograph according to claim 3, further comprising a lowest flow rate in a measurement range is equal to or less than 1 µL/min.

* * * * *